United States Patent [19]

Lenfers

[11] Patent Number: 5,562,811
[45] Date of Patent: Oct. 8, 1996

[54] DEVICE FOR TEMPERATURE MEASUREMENT AT AN OXYGEN PROBE

[75] Inventor: Martin Lenfers, Aidlingen, Germany

[73] Assignee: Robert Bosch GmbH, Stuttgart, Germany

[21] Appl. No.: 434,923

[22] Filed: May 4, 1995

[30] Foreign Application Priority Data

May 6, 1994 [DE] Germany ............... 44 15 980.3

[51] Int. Cl.⁶ ............... G01N 27/26
[52] U.S. Cl. ............... 204/408; 204/425; 204/429; 204/426; 422/94; 422/98
[58] Field of Search ............... 422/94, 95, 96, 422/98; 204/408, 425, 429, 426

[56] References Cited

U.S. PATENT DOCUMENTS

| | | | |
|---|---|---|---|
| 4,164,539 | 8/1979 | Johnston | 422/96 |
| 4,305,724 | 12/1981 | Micko | 422/94 |
| 4,579,643 | 4/1986 | Mase et al. | 204/429 |

*Primary Examiner*—Bruce F. Bell
*Attorney, Agent, or Firm*—Spencer & Frank

[57] ABSTRACT

A device for temperature measurement at an oxygen probe, in particular a lambda probe, having a solid electrolyte arranged between two electrodes. At least one of the electrodes is provided with two spaced terminals for measuring an electrical resistance of the electrodes.

16 Claims, 1 Drawing Sheet

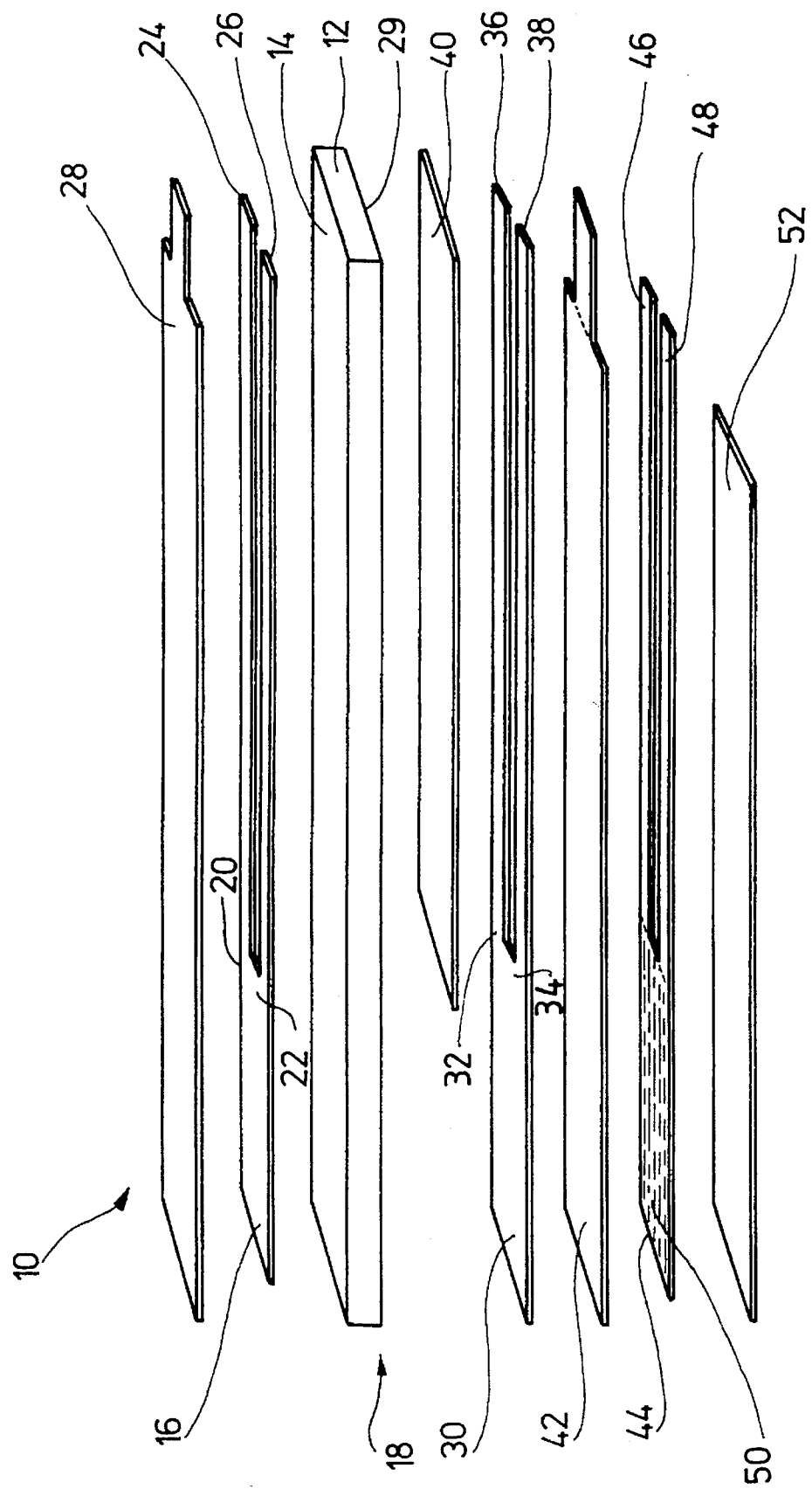

1

DEVICE FOR TEMPERATURE MEASUREMENT AT AN OXYGEN PROBE

REFERENCE TO RELATED APPLICATIONS

This application claims the priority of German application Ser. No. P 44 15 980.3, filed May 6, 1994, which is incorporated herein by reference.

BACKGROUND OF THE INVENTION

The invention relates to an arrangement for temperature measurement at an oxygen probe, in particular a lambda probe, having a solid electrolyte arranged between two electrodes.

Oxygen probes are known. They have an ionically conducting solid electrolyte located between two electrodes. The two electrodes are in this case gas-permeable and a measurement voltage can be applied to them. Depending on the oxygen content in the gas to be measured, a limit current or a Nernst voltage is set, which are dependent on the difference in the oxygen concentrations at the electrodes. Oxygen probes of this type are used, for example, as lambda probes in motor vehicles, in order to measure a specific oxygen content of the exhaust gas of internal combustion engines.

In the active range, oxygen probes must be heated to temperatures above approximately 300° C. in order to obtain the necessary ionic conductivity of the solid electrolyte. Since the signal from the oxygen probe is dependent, amongst other things, on the temperature of the oxygen probe, temperature and velocity fluctuations of the gas to be measured are frequently so large that the temperature of the measurement probe must be monitored and, if necessary, regulated in order to obtain an increase in the measurement accuracy.

In order to regulate the temperature at the measurement probe, it is known to assign to the measurement probe a probe heater which can be switched on or off as a function of a temperature measured at the oxygen probe. In this case, use is made of the effect that the internal resistance of the oxygen probe is temperature-dependent and the temperature of the oxygen probe can be deduced using the magnitude of this internal resistance. For this purpose, it is known to load the probe signal with a defined resistance and to calculate the internal resistance from the resulting load voltage. It is further known to impress an AC voltage on the probe signal using a known resistance and to calculate the AC impedance from the voltage drop across the oxygen probe. Furthermore, an alternating current of known amplitude can be superimposed on the probe signal and the AC impedance can be calculated from the reaction of the probe voltage amplitude.

In the known devices for temperature measurement, it is disadvantageous that they can be produced only at great expense using a multiplicity of components and in the end only a temperature of the solid electrolyte can be determined. However, a signal voltage from the oxygen probe is, in addition to the temperature of the solid electrolyte, dependent on a temperature difference between the measurement electrodes. This later temperature difference cannot be determined using devices known to date.

SUMMARY OF THE INVENTION

The above problems generally are solved according to the invention, by providing an oxygen probe, in particular a lambda probe, having a solid electrolyte arranged between two electrodes, wherein at least one of the two electrodes has two spaced terminals for measuring an electrical resistance of the electrodes. The oxygen probe according to the present invention has the advantage in comparison with the above known probe arrangements that determination of the temperature at the active solid electrolyte and determination of the temperature differences between the two measurement electrodes are possible. As a result of the fact that at least one of the electrodes consists of a material whose electrical resistance depends on the temperature, and this electrode has two spaced terminals for measuring an electrical resistance of the measurement electrodes, it is possible in a simple manner to arrange the electrode as part of a bridge circuit which is known per se, so that the temperature of the corresponding measurement electrode can be determined by balancing of the bridge circuit. By virtue of a corresponding geometrical arrangement of the measurement electrode, that is to say, by choice of the connection points and/or the size of the contact surface of the measurement electrode, the temperature can be determined at each position on the surface of the solid electrolyte. This temperature measurement in no way impairs operation of the oxygen probe.

According to a particularly advantageous embodiment of the invention provision is made for each of measurement electrodes to be provided with two respective spaced terminals, so that these electrodes are in each case a component or arm of a bridge circuit. A temperature difference between the measurement electrodes can thereby be determined.

Further advantageous configurations of the invention are found in the remaining features described in the application.

BRIEF DESCRIPTION OF THE DRAWINGS

The invention is explained in further detail hereinbelow in an exemplary embodiment with the aid of the associated drawings wherein the FIGURE shows an exploded representation of a limit-current probe according to the invention.

DETAILED DESCRIPTION OF THE PREFERRED EMBODIMENT

The FIGURE shows an exploded representation of a limit-current probe given the overall reference numeral 10. Only the functional parts of the limit-current probe 10 are shown in the FIGURE, while the housing and housing terminals are left out for reasons of clarity. The limit-current probe 10 has a planar, elongated body of a solid electrolyte 12 which conducts using oxygen ions and consists, for example, of stabilized zirconium dioxide. A first electrode 16 is arranged on that surface 14 of the solid electrolyte 12 which faces upward in the FIGURE. The electrode 16 consists, for example, of a porous layer of platinum. The electrode 16 is in this case formed at a front end 18 of the solid electrolyte 12, so that this electrode 16 is directly exposed to the gas to be measured.

As can be seen, the electrode 16 has two spaced terminals 20 and 22 with which contact is made by respective conductor tracks 24 and 26 extending along the remainder of the length of the solid electrolyte 12. The electrode 16 and the conductor tracks 24 and 26 may in this case be applied directly onto the surface 14 of the solid electrolyte 12 by means of a known printing technique, for example. The electrode 16 is enclosed by a cover 28. The cover 28 consists of a porous material and forms a defined diffusion resistance to the oxygen molecules in the gas to be measured. The cover 28 may, for example, be applied by pressing on zirconium dioxide, aluminum oxide or magnesium spinel and subsequent annealing. The cover 28 is arranged over the entire solid electrolyte 12 and therefore covers the electrode 16 and the conductor tracks 24 and 26. At the end remote from the exhaust gas, the cover 28 has recesses which allow contact to be made with the conductor tracks 24 and 26.

A second measurement electrode 30 is arranged opposite the electrode 16 on a surface 29 of the solid electrolyte 12 which faces downward in the FIGURE. As shown, the measurement electrode 30 likewise has two spaced terminals 32 and 34 with which contact is made by respective conductor tracks 36 and 38 extending along the remainder of the surface of the solid electrolyte 12. The measurement electrode 30 likewise consists, for example, of a porous platinum layer. An electrical insulating layer 40 is arranged between the conductor tracks 36 and 38 and surface 29 of the solid electrolyte 12. The insulating layer 40 prevents short-circuit currents between the conductor tracks 24 or 26, respectively, and the conductor tracks 36 or 38, respectively. The insulating layer 40 may, for example, consist of zirconium dioxide or aluminum oxide. The measurement electrode 30 and the conductor tracks 36 and 38 are covered by an additional insulating layer 42 which likewise consists, for example, of zirconium dioxide or aluminum oxide, but allows at least one lateral access to the measurement electrode 30 for the oxygen-containing gas to be measured. At the end remote from the gas to be measured, the insulating layer 42 has recesses which allow contact to be made with the conductor tracks 36 and 38. A heating element 44 is applied, for example, by printing, onto the insulation layer 42, with which heating element contact is made by conductor tracks 46 and 48 extending over the insulating layer 40 along the layer of the solid electrolyte 12. The heating element 44 is designed, for example, as a meandering conductor track 50 which is connected to the conductor tracks 46 and 48. The heating element 44 is provided with another cover 52 which consists of a porous material, for example zirconium dioxide or aluminum oxide. The conductor tracks 46 and 48 and the cover 52 are shortened in order to avoid a short-circuit between the conductor tracks 36 and 46 or 38 and 48, respectively and in order to make it possible to make contact with the conductor tracks 36, 38, 46 and 48. The FIGURE illustrates, solely by way of example, a limit-current probe 10 which has a height of approximately 1 mm and a width of approximately 5 mm when assembled.

During operation of the limit-current probe 10 shown in the FIGURE, it is exposed in the oxygen-containing gas to be measured, for example, to an exhaust gas of a motor vehicle. An electric voltage is applied to the electrodes 16 and 30, e.g., via the respective conductor tracks. The oxygen molecules in the gas to be measured diffuse through the electrodes 16 and 30 and the solid electrolyte 12 and are converted into oxygen ions because of the applied electric voltage. The limit current which then flows is measured by means of a measuring instrument, not shown, and provides a measure of the oxygen concentration in the gas to be measured and therefore, for example, of the adjustment of a fuel/air mixture of an internal combustion engine of a motor vehicle.

According to the invention, the electrical resistance of the electrode 16 or 30 is simultaneously measured using the conductor tracks 24 and 26 or 36 and 38, respectively. The electrodes 16 and 30 consist of a material, for example, platinum, whose resistance value changes depending on the temperature. By integrating the electrodes 16 and 30, in a simple manner, in a generally known bridge circuit (not shown), e.g., by connecting each of the electrodes in a respective arm of the bridge circuit, a change in the resistance value of the electrodes 16 or 30, respectively, can be deduced on the basis of the unbalancing of the bridge circuit. Since the resistance/temperature behavior of the electrodes 16 and 30 is known, the actual temperature existing in immediate proximity to the solid electrolyte 12 can be deduced therefrom. For sufficiently exact temperature measurement, it is per se necessary to equip one of the electrodes 16 and 30 with the two terminals and conductor tracks 24 and 26 or 36 and 38, respectively, intended for resistance measurement. However, both electrodes 16 and 30 are preferably connected, in each case to two conductor tracks, so that the temperature of the electrode 16 and the temperature of the electrode 30 can be determined independently of one another. As a result of a temperature difference occurring between the electrodes 16 and 30, which affects the signal voltage of the entire limit-current probe 10, a deviation of the signal voltage can very accurately be determined by the temperature difference, so that this deviation can accordingly be taken into account when determining the oxygen content of the gas to be measured. A very much more accurate determination of the oxygen content in the gas to be measured is therefore overall possible.

The invention now being fully described, it will be apparent to one of ordinary skill in the art that any changes and modifications can be made thereto without departing from the spirit or scope of the invention as set forth herein.

What is claimed:

1. An arrangement for temperature measurement at an oxygen probe comprising: an oxygen probe having a solid electrolyte arranged between two electrodes that have a catalytic effect, with one of said electrodes acting as an anode and the other of said electrodes acting as a cathode for generating a conduction of oxygen ions in said solid electrolyte; at least one of said electrodes having two spaced terminals; and circuit means connected to said spaced terminals of said at least one electrode for passing an electrical current through said at least one electrode and for measuring an electrical resistance of said at least one electrode to determine the temperature of said at least one electrode.

2. The arrangement as claimed in claim 1, wherein said terminals are conductor tracks.

3. The arrangement as claimed in claim 2, wherein: each of said two electrodes has two of said spaced terminals; said two conductor tracks for one of said electrodes are printed on a surface of said solid electrolyte; and said conductor tracks for the other of said electrodes are printed on an insulating material disposed on a surface of the said electrolyte and are insulated from the solid electrolyte.

4. The arrangement as claimed in claim 3, wherein said electrodes consist of a material having a temperature-dependent resistance value.

5. The arrangement as claimed in claim 4, wherein said electrodes consist of platinum.

6. The arrangement as claimed in claim 1, wherein said electrodes consist of a material having a temperature-dependent resistance value.

7. The arrangement as claimed in claim 6, wherein said electrodes consist of platinum 8. The arrangement as claimed in claim 1, wherein said circuit means comprises a bridge circuit with said at least one electrode being connected as a component of said bridge circuit.

9. The arrangement as claimed in claim 1, wherein each of said two electrodes has two of said spaced terminals; and said circuit means comprises a bridge circuit with said at least one electrode being connected as a component of said bridge circuit.

10. The probe as claimed in claim 9, wherein said terminals are conductor tracks.

11. The probe as claimed in claim 10, wherein: both of said electrodes have two of said terminals; said conductor tracks for one of said electrodes are printed on a surface of said solid electrolyte; and said conductor tracks for the other of said electrodes are insulated from said solid electrolyte.

12. The probe as claimed in claim 11, wherein said electrodes consist of a material having a temperature-dependent resistance value.

13. The probe as claimed in claim 12, wherein said electrodes consist of platinum.

14. An oxygen probe, comprising a solid electrolyte arranged between two electrodes that have a catalytic effect, with at least one of said electrodes having two spaced terminals for connection to a resistance measuring circuit whereby the electrical resistance of the at least one electrode, for a determination of its temperature, can be measured.

15. The probe as claimed in claim 14, wherein said electrodes consist of a material having a temperature-dependent resistance value.

16. The probe as claimed in claim 15, wherein said electrodes consist of platinum.

\* \* \* \* \*